United States Patent
Siriwardene

(10) Patent No.: US 11,752,043 B2
(45) Date of Patent: Sep. 12, 2023

(54) TECHNOLOGIES FOR INCONTINENCE UNDERWEAR

(71) Applicant: Thinx Inc., New York, NY (US)

(72) Inventor: Nirodha Siriwardene, New York, NY (US)

(73) Assignee: Thinx Inc., New York, NY (US)

(*) Notice: Subject to any disclaimer, the term of this patent is extended or adjusted under 35 U.S.C. 154(b) by 788 days.

(21) Appl. No.: 16/815,961

(22) Filed: Mar. 11, 2020

(65) Prior Publication Data

US 2021/0282469 A1 Sep. 16, 2021

(51) Int. Cl.
| A61F 13/15 | (2006.01) |
| A61F 13/49 | (2006.01) |
| A61F 13/494 | (2006.01) |
| A61F 13/02 | (2006.01) |

(52) U.S. Cl.
CPC .......... *A61F 13/49* (2013.01); *A61F 13/0203* (2013.01); *A61F 13/0223* (2013.01); *A61F 13/494* (2013.01); *A61F 13/49006* (2013.01); *A61F 13/49406* (2013.01); *A61F 13/49426* (2013.01); *A61F 2013/15487* (2013.01); *A61F 2013/15991* (2013.01); *A61F 2250/0076* (2013.01)

(58) Field of Classification Search
CPC ........ A61F 13/539; A61F 13/47; A61F 13/51; A61F 13/49; A61F 13/0203; A61F 13/0223; A61F 13/49006; A61F 13/494; A61F 13/49406; A61F 13/49426; A61F 2013/15487; A61F 2013/15991; A61F 2250/0076
See application file for complete search history.

(56) References Cited

U.S. PATENT DOCUMENTS

| 2,853,073 A | 9/1958 | Lena |
| 5,306,267 A | 4/1994 | Hahn |
| 5,669,902 A | 9/1997 | Sivilich |
| 5,993,433 A | 11/1999 | St. Louis |
| 11,395,774 B2* | 7/2022 | Skinner ................ A61F 13/539 |
| 2002/0032422 A1 | 3/2002 | Goyarts |
| 2011/0152814 A1 | 6/2011 | Seneviratne |
| 2014/0039432 A1* | 2/2014 | Dunbar .................. A61F 13/66 604/394 |

FOREIGN PATENT DOCUMENTS

WO WO9321878 11/1993

OTHER PUBLICATIONS

International Search Report dated May 21, 2021 for PCT/US2021/021626 filed Mar. 10, 2021 (12 pages).

* cited by examiner

*Primary Examiner* — Jacqueline F Stephens
(74) *Attorney, Agent, or Firm* — Dentons US LLP

(57) ABSTRACT

An incontinence underwear including a crotch area hosting a stitching, a first layer, a second layer, a third layer, a fourth layer, a fifth layer, a sixth layer, and a seventh layer, wherein the first layer is innermost, wherein the seventh layer is outermost, wherein the second layer extends between the first layer and the third layer, wherein the fourth layer extends between the third layer and the fifth layer, wherein the sixth layer extends between the fifth layer and the seventh layer, wherein the stitching extends through the first layer, the second layer, the sixth layer, and the seventh layer, wherein the stitching avoids extending through the third layer, the fourth layer, and the fifth layer, wherein the second layer is bonded or adhered to the third layer.

17 Claims, 9 Drawing Sheets

TECHNOLOGIES FOR INCONTINENCE UNDERWEAR

TECHNICAL FIELD

This disclosure relates to incontinence underwear.

BACKGROUND

In this disclosure, where a document, an act, and/or an item of knowledge is referred to and/or discussed, then such reference and/or discussion is not an admission that the document, the act, and/or the item of knowledge and/or any combination thereof was at a priority date, publicly available, known to a public, part of common general knowledge, and/or otherwise constitutes any prior art under any applicable statutory provisions; and/or is known to be relevant to any attempt to solve any problem with which this disclosure is concerned with. Further, nothing is disclaimed.

There is a desire to enable an incontinence underwear that is sufficiently waterproof, yet adequately resistant to wear and tear. However, despite various attempts by others, this type of incontinence underwear does not yet exist. As such, this disclosure enables such type of incontinence underwear.

SUMMARY

This disclosure at least partially addresses at least one of above inefficiencies. However, this disclosure can prove useful to other technical areas. Therefore, various claims recited below should not be construed as necessarily limited to addressing any of the above inefficiencies.

According to an embodiment of this disclosure, a device comprises: an incontinence underwear including a crotch area hosting a stitching, a first layer, a second layer, a third layer, a fourth layer, a fifth layer, a sixth layer, and a seventh layer, wherein the first layer is innermost, wherein the seventh layer is outermost, wherein the second layer extends between the first layer and the third layer, wherein the fourth layer extends between the third layer and the fifth layer, wherein the sixth layer extends under the fifth layer and above the seventh layer, wherein the stitching extends through the first layer, the second layer, the sixth layer, and the seventh layer, wherein the stitching avoids extending through the third layer, the fourth layer, and the fifth layer, wherein the second layer is bonded or adhered to the third layer.

The device according to one of the prior embodiments, wherein the second layer is adhered or bonded to the first layer.

The device according to one of the prior embodiments, wherein the second layer is adhered or bonded to the sixth layer.

The device according to one of the prior embodiments, wherein the first layer is coupled to the sixth layer via the second layer.

The device according to one of the prior embodiments, further comprising a bonding strip that extend from below the fifth layer to above the third layer along the entire peripheries of the third layer, the fourth layer and the fifth layer.

According to an embodiment of this disclosure, a method comprises: causing an incontinence underwear to include a crotch area hosting a stitching, a first layer, a second layer, a third layer, a fourth layer, a fifth layer, a sixth layer, and a seventh layer, wherein the first layer is innermost, wherein the seventh layer is outermost, causing the second layer to extend between the first layer and the third layer such that the second layer is bonded or adhered to the third layer; causing the fourth layer to extend between the third layer and the fifth layer; causing the sixth layer to extend below the fifth layer and above the seventh layer; causing the stitching to extend through the first layer, the second layer, the sixth layer, and the seventh layer and avoid extending through the third layer, the fourth layer, and the fifth layer.

The method according to one of the prior embodiments, wherein the second layer is adhered or bonded to the first layer.

The method according to one of the prior embodiments, wherein the second layer is adhered or bonded to the sixth layer.

The method according to one of the prior embodiments, wherein the first layer is coupled to the sixth layer via the second layer.

The method according to one of the prior embodiments, further comprising coupling a bonding strip that extend from below the fifth layer to above the third layer along the entire peripheries of the third layer, the fourth layer and the fifth layer.

This disclosure is embodied in various forms illustrated in a set of accompanying illustrative drawings. Note that variations are contemplated as being a part of this disclosure, limited only by a scope of various claims recited below.

DESCRIPTION OF DRAWINGS

The set of accompanying illustrative drawings shows various example embodiments of this disclosure. Such drawings are not to be construed as necessarily limiting this disclosure. Like numbers and/or similar numbering scheme can refer to like and/or similar elements throughout.

DETAILED DESCRIPTION OF PREFERRED EMBODIMENTS

Figure 1:
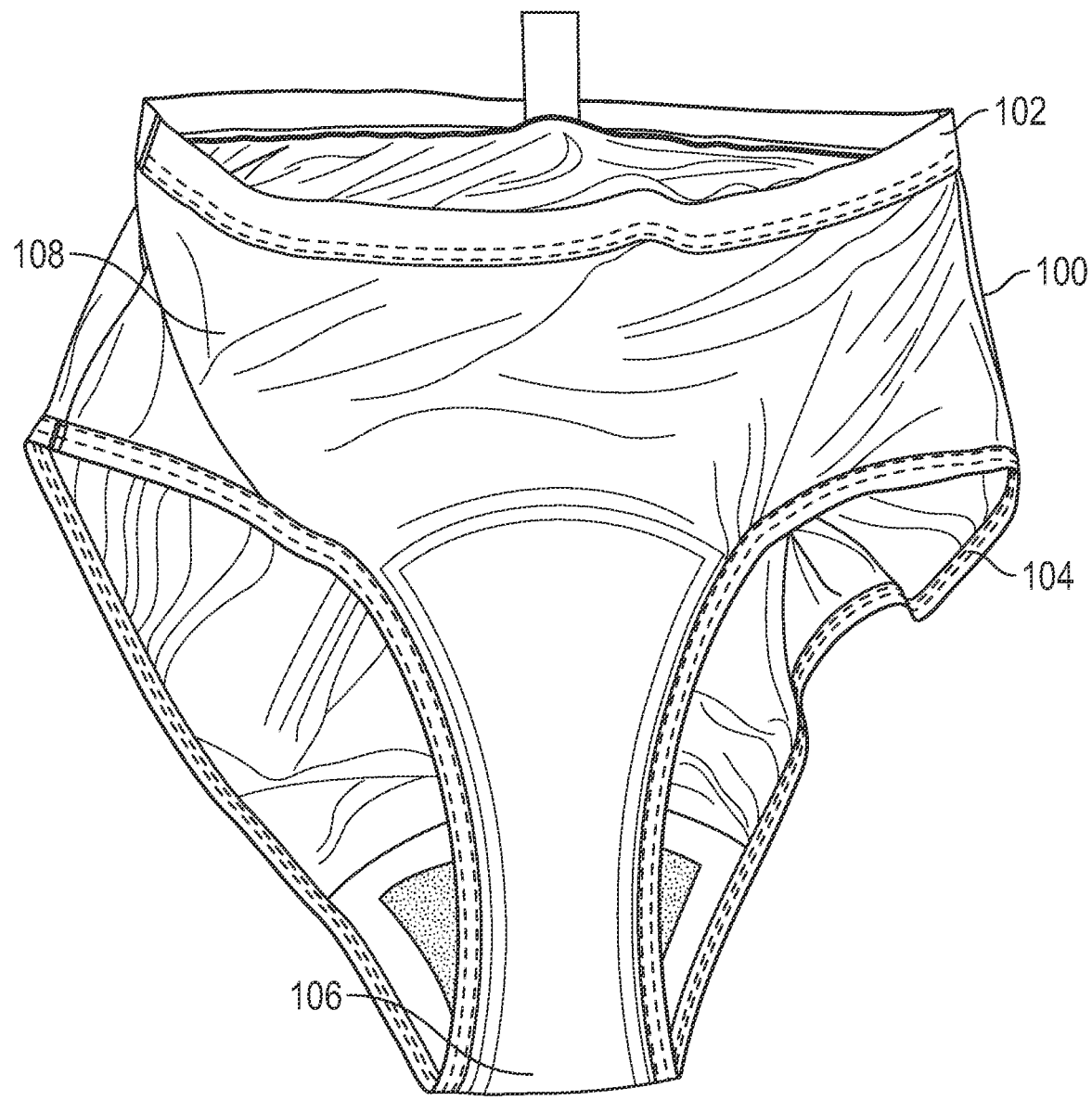
FIGS. 1-7 show various perspective views of an incontinence underwear according to this disclosure.

This disclosure is now described more fully with reference to the set of accompanying illustrative drawings, in which example embodiments of this disclosure are shown. This disclosure can be embodied in many different forms and should not be construed as necessarily being limited to the example embodiments disclosed herein. Rather, the example embodiments are provided so that this disclosure is thorough and complete, and fully conveys various concepts of this disclosure to those skilled in a relevant art.

Features described with respect to certain example embodiments can be combined and sub-combined in and/or with various other example embodiments. Also, different aspects and/or elements of example embodiments, as disclosed herein, can be combined and sub-combined in a similar manner as well. Further, some example embodiments, whether individually and/or collectively, can be components of a larger system, wherein other procedures can take precedence over and/or otherwise modify their application. Additionally, a number of steps can be required before, after, and/or concurrently with example embodiments, as disclosed herein. Note that any and/or all methods and/or processes, at least as disclosed herein, can be at least partially performed via at least one entity in any manner.

Various terminology used herein can imply direct or indirect, full or partial, temporary or permanent, action or inaction. For example, when an element is referred to as being "on," "connected" or "coupled" to another element, then the element can be directly on, connected or coupled to the other element and/or intervening elements can be present, including indirect and/or direct variants. In contrast, when an element is referred to as being "directly connected" or "directly coupled" to another element, there are no intervening elements present.

Although the terms first, second, etc. can be used herein to describe various elements, components, regions, layers and/or sections, these elements, components, regions, layers and/or sections should not necessarily be limited by such terms. These terms are used to distinguish one element, component, region, layer or section from another element, component, region, layer or section. Thus, a first element, component, region, layer, or section discussed below could be termed a second element, component, region, layer, or section without departing from various teachings of this disclosure.

Various terminology used herein is for describing particular example embodiments and is not intended to be necessarily limiting of this disclosure. As used herein, various singular forms "a," "an" and "the" are intended to include various plural forms as well, unless a context clearly indicates otherwise. Various terms "comprises," "includes" and/or "comprising," "including" when used in this specification, specify a presence of stated features, integers, steps, operations, elements, and/or components, but do not preclude the presence and/or addition of one or more other features, integers, steps, operations, elements, components, and/or groups thereof.

As used herein, a term "or" is intended to mean an inclusive "or" rather than an exclusive "or." That is, unless specified otherwise, or clear from context, "X employs A or B" is intended to mean any of a set of natural inclusive permutations. That is, if X employs A; X employs B; or X employs both A and B, then "X employs A or B" is satisfied under any of the foregoing instances.

Example embodiments of this disclosure are described herein with reference to illustrations of idealized embodiments (and intermediate structures) of this disclosure. As such, variations from various illustrated shapes as a result, for example, of manufacturing techniques and/or tolerances, are to be expected. Thus, various example embodiments of this disclosure should not be construed as necessarily limited to various particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing, and/or other any other types of manufacturing. For example, some manufacturing processes include three dimensional (3D) printing, laser cutting, computer numerical control routing, milling, pressing, stamping, vacuum forming, hydroforming, injection molding, lithography, and so forth.

Any and/or all elements, as disclosed herein, can be and/or include, whether partially and/or fully, a solid, including a metal, a mineral, an amorphous material, a ceramic, a glass ceramic, an organic solid, such as wood and/or a polymer, such as rubber, a composite material, a semiconductor, a nanomaterial, a biomaterial and/or any combinations thereof. Any and/or all elements, as disclosed herein, can be and/or include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, opaqueness, luminescence, reflection, phosphorescence, anti-reflection and/or holography, a photo-sensitive coating, an electronic and/or thermal property coating, such as for passivity, insulation, resistance or conduction, a magnetic coating, a water-resistant and/or waterproof coating, a scent coating and/or any combinations thereof. Any and/or all elements, as disclosed herein, can be rigid, flexible, and/or any other combinations thereof. Any and/or all elements, as disclosed herein, can be identical and/or different from each other in material, shape, size, color and/or any measurable dimension, such as length, width, height, depth, area, orientation, perimeter, volume, breadth, density, temperature, resistance, and so forth.

Unless otherwise defined, all terms (including technical and scientific terms) used herein have the same meaning as commonly understood by one of ordinary skill in an art to which this disclosure belongs. Various terms, such as those defined in commonly used dictionaries, should be interpreted as having a meaning that is consistent with a meaning in a context of a relevant art and should not be interpreted in an idealized and/or overly formal sense unless expressly so defined herein.

Furthermore, relative terms such as "below," "lower," "above," and "upper" can be used herein to describe one element's relationship to another element as illustrated in the set of accompanying illustrative drawings. Such relative terms are intended to encompass different orientations of illustrated technologies in addition to an orientation depicted in the set of accompanying illustrative drawings. For example, if a device in the set of accompanying illustrative drawings were turned over, then various elements described as being on a "lower" side of other elements would then be oriented on "upper" sides of other elements. Similarly, if a device in one of illustrative figures were turned over, then various elements described as "below" or "beneath" other elements would then be oriented "above" other elements. Therefore, various example terms "below" and "lower" can encompass both an orientation of above and below.

As used herein, a term "about" and/or "substantially" refers to a +/−10% variation from a nominal value/term. Such variation is always included in any given value/term provided herein, whether or not such variation is specifically referred thereto.

If any disclosures are incorporated herein by reference and such disclosures conflict in part and/or in whole with this disclosure, then to an extent of a conflict, if any, and/or a broader disclosure, and/or broader definition of terms, this disclosure controls. If such disclosures conflict in part and/or in whole with one another, then to an extent of a conflict, if any, a later-dated disclosure controls.

Figure 8:
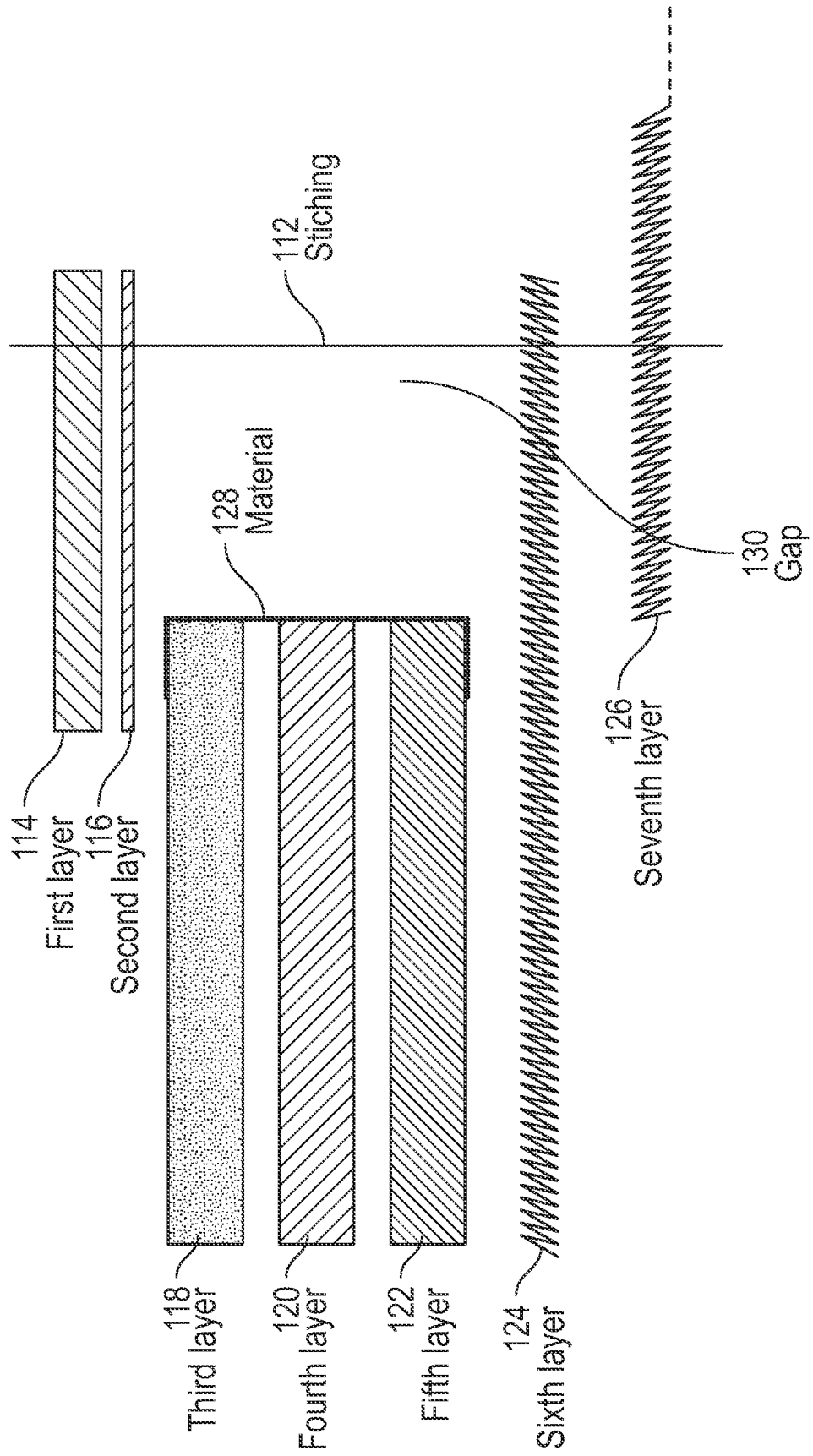
FIG. 8 shows a cross-sectional view of a crotch area of the incontinence underwear according to an embodiment of this disclosure.

FIGS. 1-7 show various perspective views of an incontinence underwear according to this disclosure. FIG. 8 shows a cross-sectional view of a crotch area of the incontinence underwear according to this disclosure. In particular, an incontinence underwear 100 includes a waistband 102, a front area 108, a back area 110, and a pair of leg openings 104 that define a crotch area 106 therebetween, any of which can include any suitable material (e.g., fabric, natural yarn, synthetic yarn, cotton, silk, polyester, spandex, rubber, plastic, metal, merino wool, nylon, polypropylene, rayon, linen, spandex, bamboo, Gore-Tex, X-static, tencel).

Figure 2:
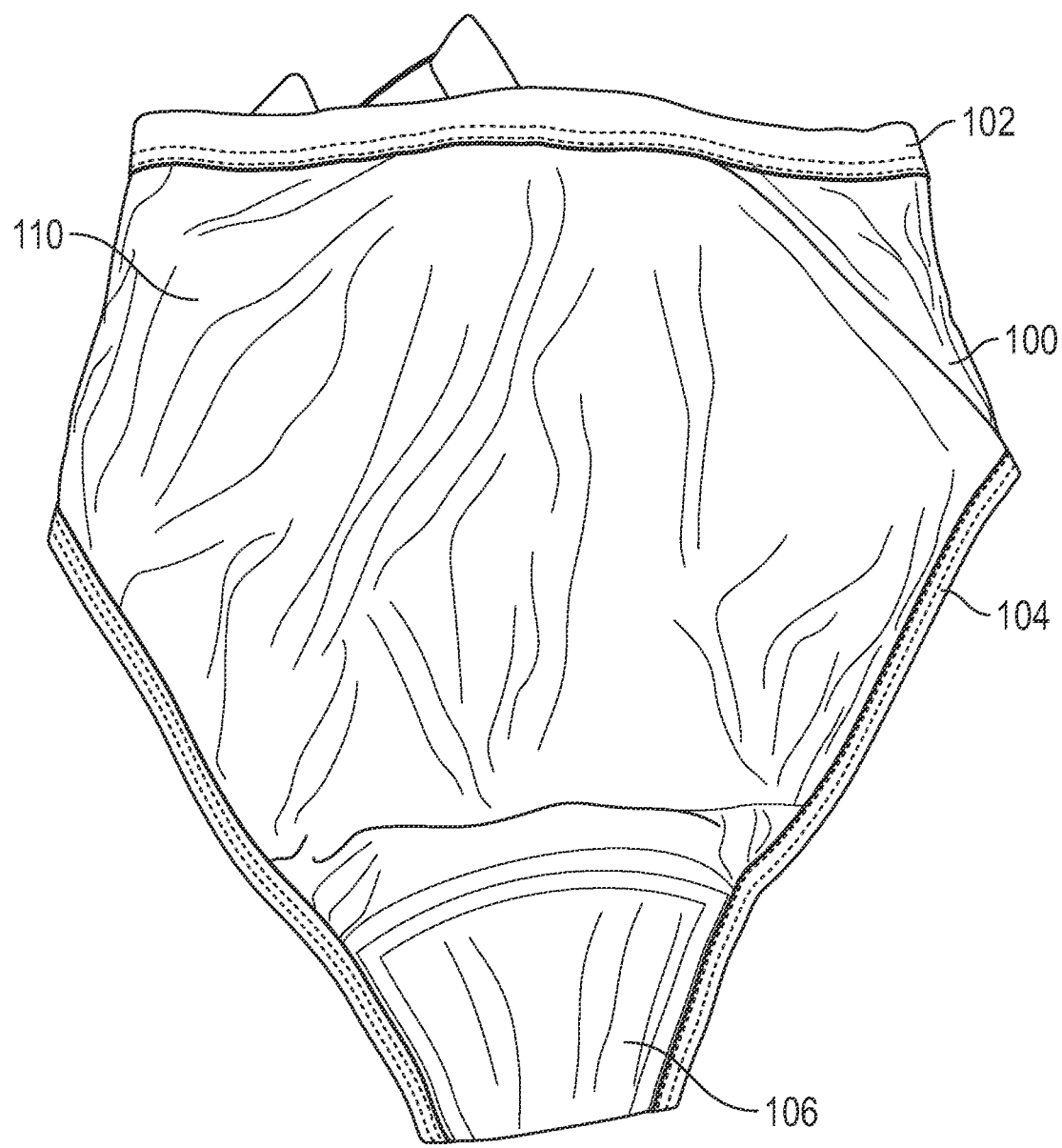
Figure 3:
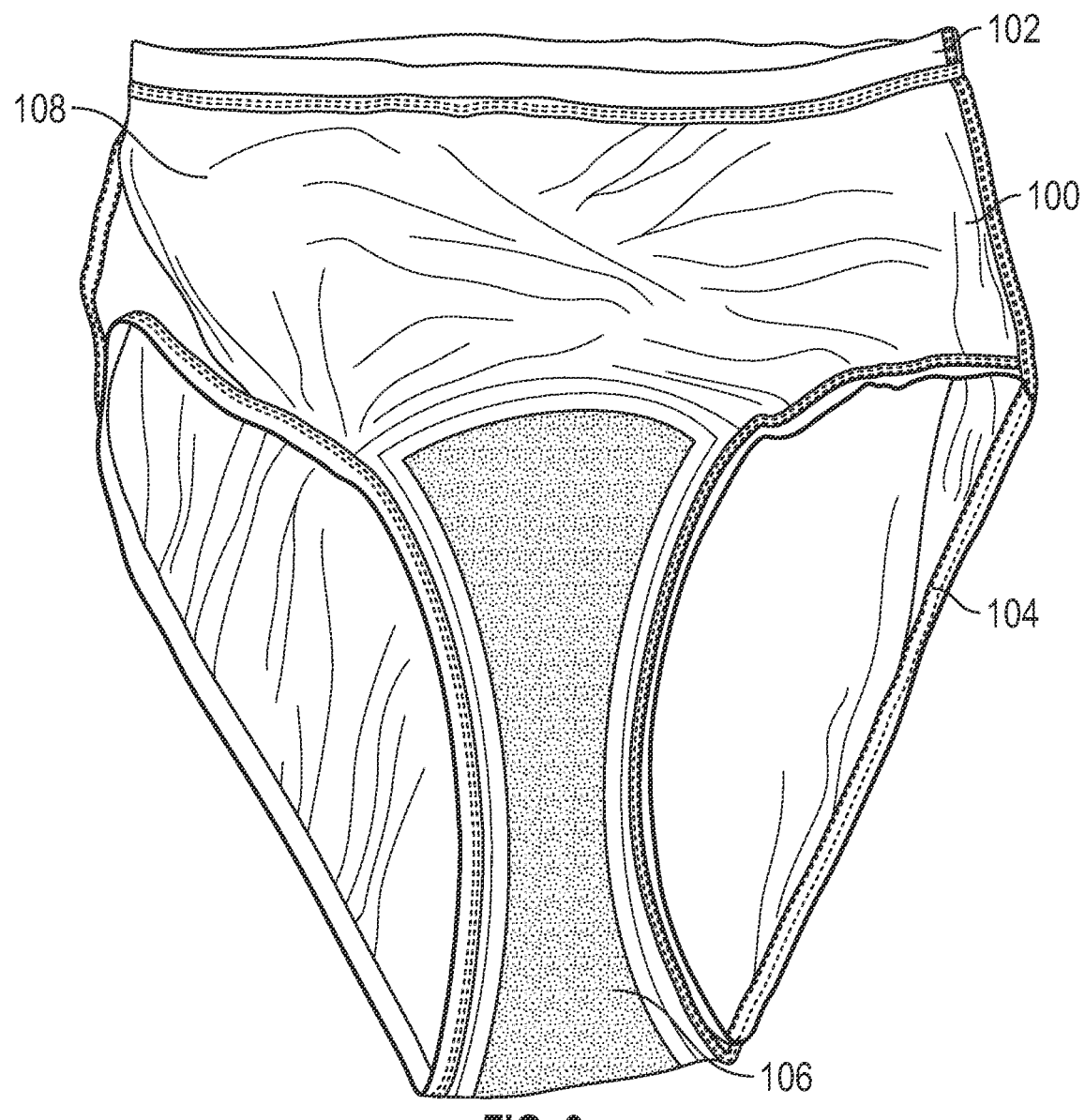
Figure 4:
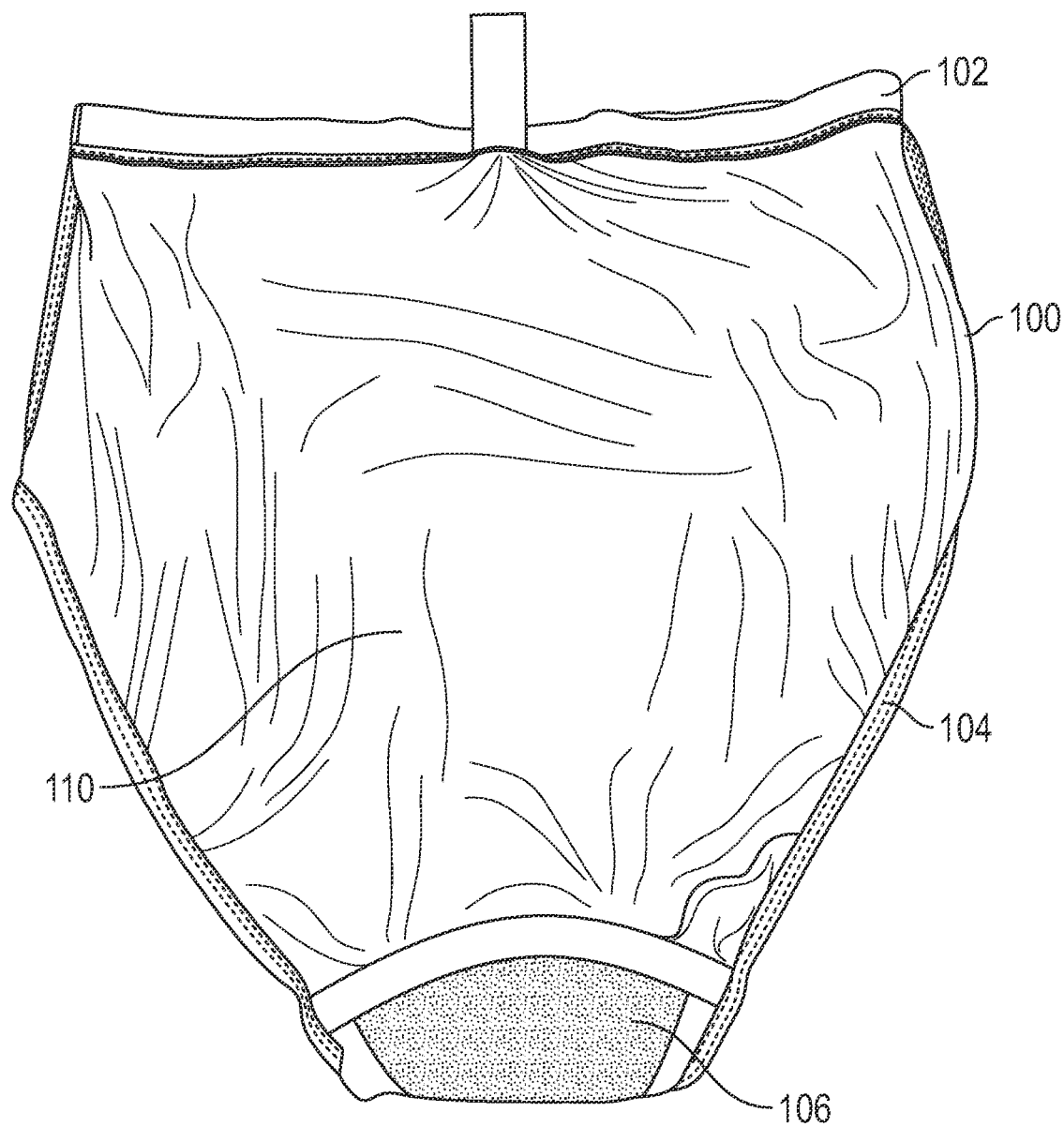

As shown in FIGS. 1 and 2, the underwear 100 includes an external side (distal to wearer's body) having the waistband 102, the front area 108, the back area 110, the pair of leg openings 104, and the crotch area 106. Likewise, as shown in FIGS. 3 and 4, the underwear 100 includes an internal side (proximal to wearer's body) having the waistband 102, the front area 108, the back area 110, the pair of leg openings 104, and the crotch area 106.

As shown in FIGS. 3-8, the crotch area 106 hosts a stitching 112, a first layer 114, a second layer 116, a third layer 118, a fourth layer 120, a fifth layer 122, a sixth layer 124, a seventh layer 126, and a material 128, any of which can include any suitable material (e.g., fabric, natural yarn, synthetic yarn, cotton, silk, polyester, spandex, rubber, plastic, metal, merino wool, nylon, polypropylene, rayon, linen, spandex, bamboo, Gore-Tex, X-static, tencel). The first layer 114 is innermost. The seventh layer 126 is outermost. Alternatively, the sixth layer 124 is outermost. The second layer 116 extends between the first layer 114 and the third layer 118. The fourth layer 120 extends between the third layer 118 and the fifth layer 122. The sixth layer 124 extends below the fifth layer 122 and above the seventh layer 126.

The third layer 118 includes a moisture-wicking material (e.g., fabric, natural yarn, synthetic yarn, wool, polypropylene, nylon, polyester). Alternatively, the fourth layer 120 or the fifth layer 122 may include moisture-wicking material. The fourth layer 120 includes an absorbent material (e.g., fabric, natural yarn, synthetic yarn, wool, polypropylene, nylon, polyester). Alternatively, the third layer 118 or the fifth layer 122 includes an absorbent material. The fifth layer 122 includes a waterproof material (can be a coating), but water resistant or water repellant material (can be a coating) can be included as well. Alternatively, the third layer 118 or the fourth layer 120 can include a waterproof material. The second layer 116 includes or comprises a bonding tape (e.g., strip).

Figure 9:
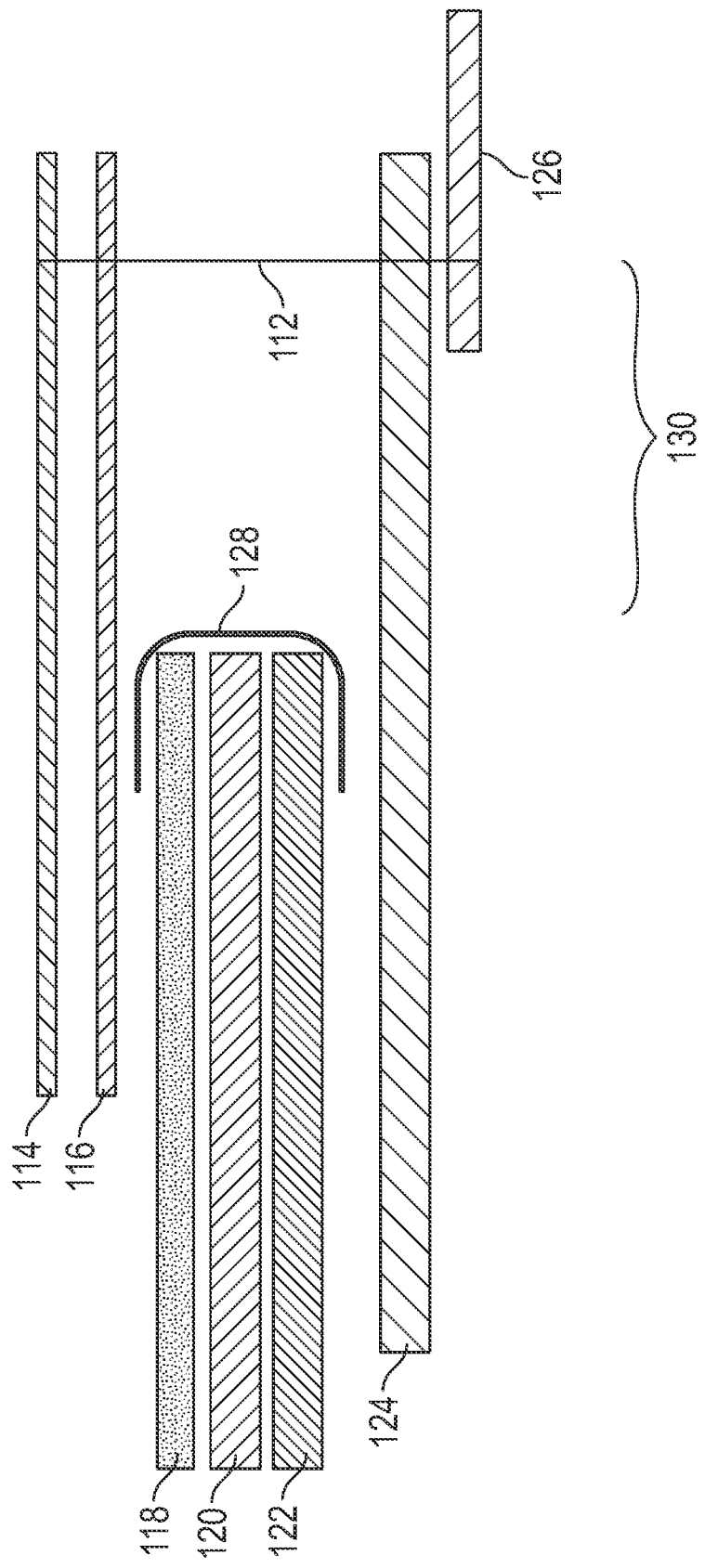
FIG. 9 shows a cross-sectional view of a crotch area of the incontinence underwear according to an embodiment of this disclosure.

As shown in FIG. 9, the stitching 112 extends through the first layer 114, the second layer 116, the sixth layer 124, and the seventh layer 126. The stitching 112 avoids extending through the third layer 118, the fourth layer 120, and the fifth layer 122.

The second layer 116 is bonded or adhered to the third layer 118. In certain embodiments, the second layer 116 is bonded or adhered to sixth layer 124. For example, such bonding can be via a suitable bonding tape (e.g., strip). Likewise, for example, such adhering can be via a suitable adhesive (e.g., glue). In certain embodiments, the second layer 116 comprises bonding tape or glue.

In certain embodiments, the edges of at least two of the third layer 118, the fourth layer 120, or the fifth layer 120 are encapsulated via material 128 that extends between the second layer 116 and the sixth layer 124. The material 128 is U-shaped or C-shaped, but other shapes are possible (e.g., V-shape). The material 128 encapsulates the edges of the third layer 118, the fourth layer 120, and the fifth layer 122, although the material 128 can encapsulate other layers or at least one of the third layer 118, the fourth layer 120, and the fifth layer 122.

The encapsulation may be achieved, for example, by extending the material 128 from below the fifth layer 122 to above the third layer 118 and around the peripheries of the third layer 118, the fourth layer 120 and the fifth layer 122, and binding the material 128 to an upper portion of the third layer 118 and to a lower portion of the fifth layer 122. The material 128 extends between the second layer 116 and the third layer 118, and between the fifth layer 122 and the sixth layer 124.

In certain embodiments, the second layer 116 is bonded (e.g., bonding tape) or adhered (e.g., adhesive, glue) to the third layer 118 via the material 128. In certain embodiments, bonding tape or glue, other than material 128, is used to bond or adhere the second layer 116 to the third layer. In certain embodiments, the second layer 116 comprises bonding tape or glue and the first layer 114 is coupled to the third layer 118 via the second layer 116.

In certain embodiments, the second layer 116 directly contacts the first layer 114 and the third layer 118. In certain embodiments, the second layer 116 directly contacts the first layer 114 and the material 128. In certain embodiments, the second layer 116 directly contacts the first layer 114, the third layer 118 and the material 128.

As shown in FIGS. 8-9, the material 128 and the stitching 112 define a gap 130 therebetween. The gap 130 extends between the second layer 116 and the sixth layer 124. The gap 130 can have any volumetric shape. Therefore, since the second layer 116 extends between the first layer 114 and the third layer 118 at a first point and the stitching 112 extends through the second layer 116 at a second point, then the first point is spaced apart from the second point (e.g., between about 0.001 inch and 3 inches).

In certain embodiments, the first layer 114 and the second layer 116 define an elastic edge portion. In certain embodiments, the sixth layer 124 and the seventh layer 126 define an elastic edge portion. For example, the elastic edge portion can include rubber or any other suitable materials (e.g., fabric, natural yarn, synthetic yarn, cotton, silk, polyester, spandex, rubber, plastic, metal, merino wool, nylon, polypropylene, rayon, linen, spandex, bamboo, Gore-Tex, X-static, spandex, tencel).

Figure 5:
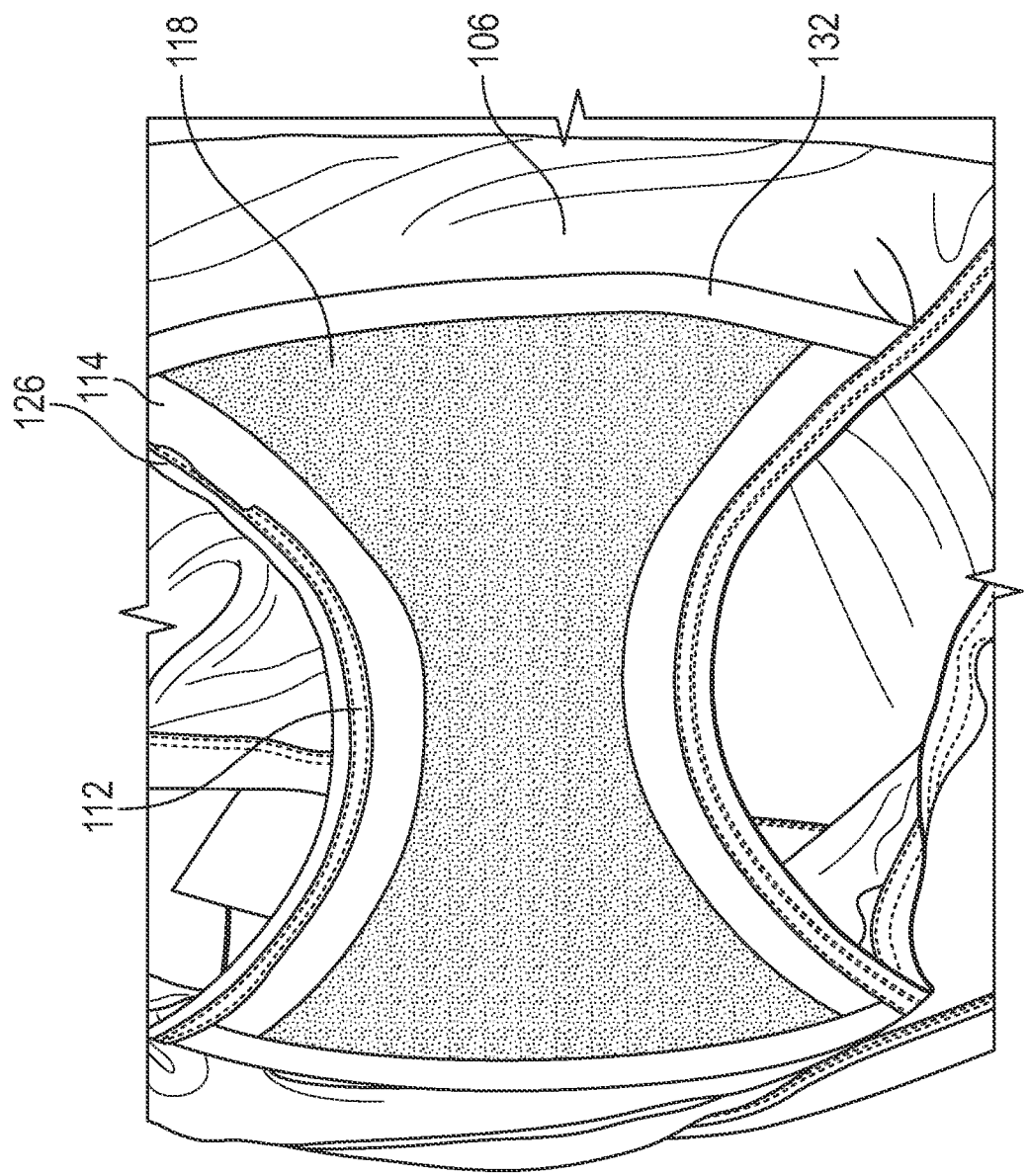
Figure 6:
Figure 7:
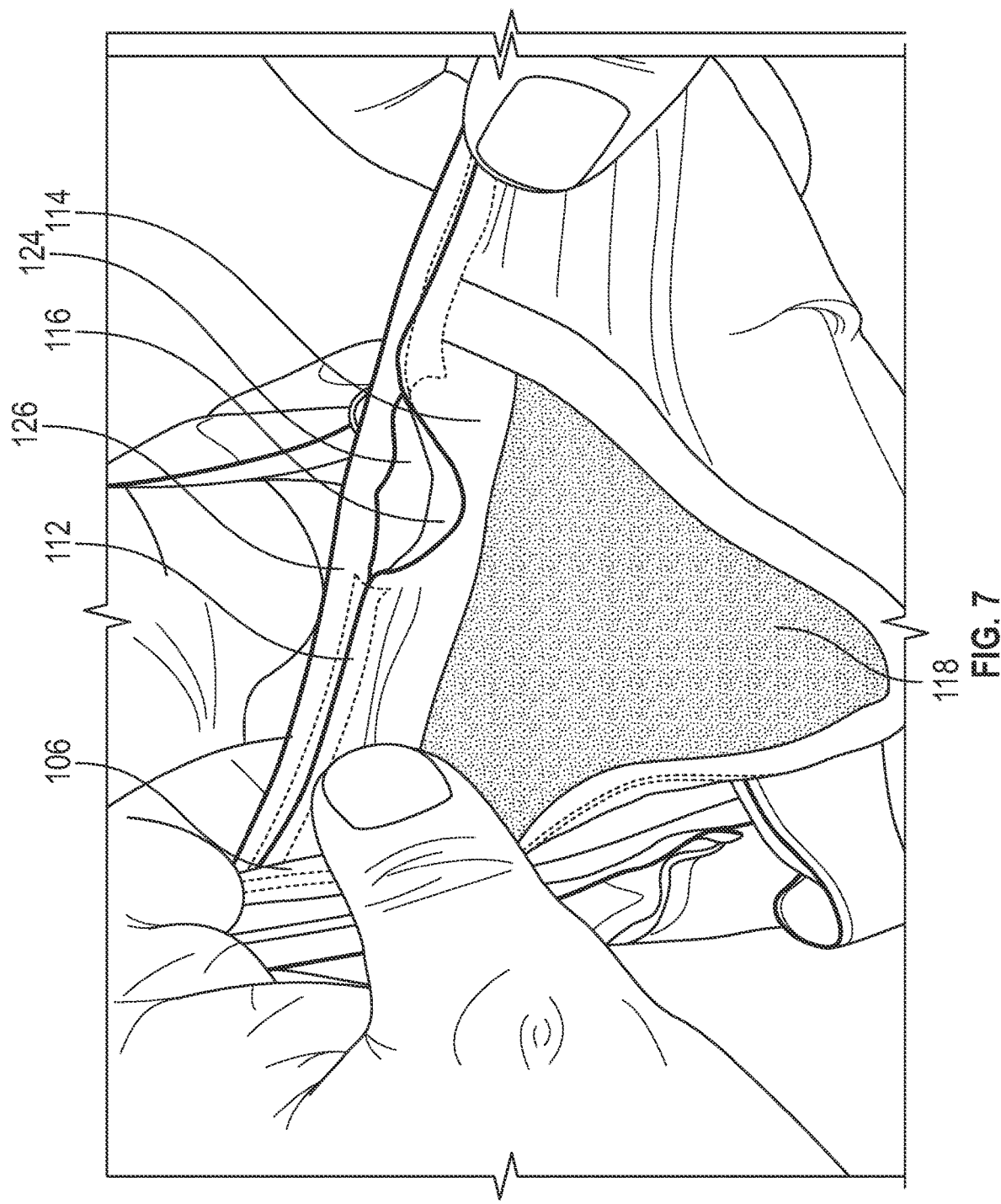

As shown in FIG. 5, the first layer 114 defines a bow shaped area 132 through which the third layer 118 is presented as bow shaped. The third layer 118 is visually distinct relative to the first layer 114, but can avoid being visually distinct. Note that the bow shaped area 132 is not limited to being bow shaped and other shapes or shape patterns are possible (e.g., triangular, circular, rectangular, square, octagon, pentagon, hexagon, pentagonal or hexagonal star, rhombus, polka dot).

In one mode of operation, a method can include: causing the incontinence underwear 100 to include the crotch area 106 hosting the stitching 112, the first layer 114, the second layer 116, the third layer 118, the fourth layer 120, the fifth layer 122, the sixth layer 124, and the seventh layer 126. The first layer 114 is innermost and the seventh layer 126 is outermost. The method can include causing the second layer 116 to extend between the first layer 114 and the third layer 118 such that the second layer 116 is bonded or adhered to the third layer 118. The method can include causing the fourth layer 120 to extend between the third layer 118 and the fifth layer 122. The method can include causing the sixth layer 124 to extend between the fifth layer 122 and the seventh layer 126. The method can include causing the stitching 112 to extend through the first layer 114, the second layer 116, the sixth layer 124, and the seventh layer 126 and avoid extending through the third layer 118, the fourth layer 120, and the fifth layer 122. As such, at least a portion of the crotch area can be absorbent and leak-proof (e.g. water, bodily fluid, blood, urine, feces).

In one mode of operation, the third layer 118 wicks moisture (e.g., fabric, natural yarn, synthetic yarn, wool, polypropylene, nylon, polyester). Alternatively, the fourth layer 120 or the fifth layer 122 may wick moisture. The fourth layer 120 absorbs moisture (e.g., fabric, natural yarn, synthetic yarn, wool, polypropylene, nylon, polyester). Alternatively, the third layer 118 or the fifth layer 122 absorb moisture. The fifth layer 122 prevents transfer of moisture (can be a coating). Alternatively, the third layer 118 or the fourth layer 120 prevent transfer of moisture. The second layer 116 includes or comprises a bonding tape (e.g., strip).

According to one mode of operation, as shown in FIG. 9, the method can include causing the stitching 112 to extend through the first layer 114, the second layer 116, the sixth layer 124, and the seventh layer 126. According to one mode of operation, the method can include avoiding the stitching 112 from extending through the third layer 118, the fourth layer 120, and the fifth layer 122.

In certain embodiments, the method can include bonding or adhering the second layer 116 to the third layer 118. In certain embodiments, the method can include bonding or adhering the second layer 116 to the sixth layer 124. For example, such bonding can be via a suitable bonding tape (e.g., strip). Likewise, for example, such adhering can be via a suitable adhesive (e.g., glue). In certain embodiments, the second layer 116 comprises bonding tape or glue.

In certain embodiments, the method can include encapsulating at least two of the third layer 118, the fourth layer 120, or the fifth layer 120 via material 128 that extends between the second layer 116 and the sixth layer 124. The material 128 is U-shaped or C-shaped, but other shapes are possible (e.g., V-shape). The method can include material 128 encapsulating the third layer 118, the fourth layer 120, and the fifth layer 122, although the material 128 can encapsulate other layers or at least one of the third layer 118, the fourth layer 120, and the fifth layer 122.

The encapsulation may be achieved, for example, by extending the material 128 from below the fifth layer 122 to above the third layer 118 and around the periphery of the third layer 118, the fourth layer 120 and the fifth layer 122, and binding the material 128 to an upper portion of the third layer 118 and to a lower portion of the fifth layer 122. The material 128 extends between the second layer 116 and the third layer 118, and between the fifth layer 122 and the sixth layer 124.

In certain embodiments, the method can include bonding (e.g., bonding tape) or adhering (e.g., adhesive, glue) the second layer 116 to the third layer 118 via the material 128. In certain embodiments, bonding tape or glue, other than material 128, is used to bond or adhere the second layer 116 to the third layer. In certain embodiments, the second layer 116 comprises bonding tape or glue and coupling the first layer 114 to the third layer 118 via the second layer 116.

In certain embodiments, the method can include directly contacting the second layer 116 to the first layer 114 and the third layer 118. In certain embodiments, the method can include directly contacting the second layer 116 with the first layer 114 and the material 128. In certain embodiments, the method can include directly contacting the second layer 116 with the first layer 114, the third layer 118 and the material 128.

As shown in FIGS. 8-9, the method can include including a gap 130 between the material 128 and the stitching 112. The method can include extending the gap 130 between the second layer 116 and the sixth layer 124. The gap 130 can have any volumetric shape. Therefore, since the second layer 116 is extended between the first layer 114 and the third layer 118 at a first point and the stitching 112 is extended through the second layer 116 at a second point, then the first point is spaced apart from the second point (e.g., between about 0.001 inch and 3 inches).

In certain embodiments, the method can include the first layer 114 and the second layer 116 defining an elastic edge portion. In certain embodiments, the method can include the sixth layer 124 and the seventh layer 126 defining an elastic edge portion. For example, the elastic edge portion can include rubber or any other suitable materials (e.g., fabric, natural yarn, synthetic yarn, cotton, silk, polyester, spandex, rubber, plastic, metal, merino wool, nylon, polypropylene, rayon, linen, spandex, bamboo, Gore-Tex, X-static, spandex, tencel).

As shown in FIG. 5, the first layer 114 defines a bow shaped area 132 through which the third layer 118 is presented as bow shaped. The third layer 118 is visually distinct relative to the first layer 114, but can avoid being visually distinct. Note that the bow shaped area 132 is not limited to being bow shaped and other shapes or shape patterns are possible (e.g., triangular, circular, rectangular, square, octagon, pentagon, hexagon, pentagonal or hexagonal star, rhombus, polka dot).

In some embodiments, the incontinence underwear 100 can be embodied as disclosed in US20160089276, EP2879534, US20180014983, US20180092787, JP3718213, all of which are incorporated by reference herein for all purposes. As such, any of such references can be modified based on this disclosure using various principles, as known to skilled artisans in this technical field.

In some embodiments, various functions or acts can take place at a given location and/or in connection with the operation of one or more apparatuses or systems. In some embodiments, a portion of a given function or act can be performed at a first device or location, and a remainder of the function or act can be performed at one or more additional devices or locations.

The corresponding structures, materials, acts, and equivalents of all means or step plus function elements in the claims below are intended to include any structure, material, or act for performing the function in combination with other claimed elements as specifically claimed. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the steps can be performed in a differing order or steps can be added, deleted or modified. All of these variations are considered a part of the disclosure. It will be understood that those skilled in the art, both now and in the future, can make various improvements and enhancements which fall within the scope of the claims which follow.

The description of this disclosure has been presented for purposes of illustration and description, but is not intended to be fully exhaustive and/or limited to the disclosure in the form disclosed. Many modifications and variations in techniques and structures will be apparent to those of ordinary skill in an art without departing from a scope and spirit of this disclosure as set forth in the claims that follow. Accordingly, such modifications and variations are contemplated as being a part of this disclosure. A scope of this disclosure is defined by various claims, which include known equivalents and unforeseeable equivalents at a time of filing of this disclosure.

The invention claimed is:

1. A device comprising:
an incontinence underwear including a crotch area hosting a stitching, a first layer, a second layer, a third layer, a fourth layer, a fifth layer, a sixth layer, and a seventh layer, wherein the crotch area is adjacent to a first leg opening and a second leg opening,
wherein the first layer is innermost, wherein the seventh layer is outermost, wherein the second layer extends between the first layer and the third layer, wherein the fourth layer extends between the third layer and the fifth layer, wherein the sixth layer extends between the fifth layer and the seventh layer, wherein the stitching extends through the first layer, the second layer, the sixth layer, and the seventh layer, wherein the stitching avoids extending through the third layer, the fourth layer, and the fifth layer, wherein the second layer is bonded or adhered to the third layer,
wherein the third layer comprises a center portion and a peripheral edge portion surrounding the center portion, wherein a first section of the peripheral edge portion is adjacent to the first leg opening and a second section of the peripheral edge portion is adjacent to the second leg opening, wherein the first layer overlays the first section of the peripheral edge portion and the second section of the peripheral edge portion, and wherein the first layer does not overlay the center portion.

2. The device of claim 1, wherein the fifth layer is bonded or adhered to the sixth layer.

3. The device of claim 1, wherein the third layer, the fourth layer, or the fifth layer includes a moisture-wicking material.

4. The device of claim 1, wherein the third layer, the fourth layer, or the fifth layer includes a waterproof material.

5. The device of claim 1, wherein the second layer includes a bonding tape.

6. The device of claim 1, wherein the second layer extends between the first layer and the third layer at a first point, wherein the stitching extends through the second layer at a second point, wherein the first point is spaced apart from the second point.

7. The device of claim 1, wherein the sixth layer and the seventh layer define an elastic edge portion.

8. The device of claim 1, wherein the first layer defines a bow shaped area through which the third layer is presented as bow shaped.

9. The device of claim 1, wherein the third layer is visually distinct relative to the first layer.

10. The device of claim 1, wherein the second layer directly contacts the first layer and the third layer.

11. The device of claim 1, wherein the second layer directly contacts the first layer and a material encapsulating the third layer.

12. A device comprising, an incontinence underwear including a crotch area hosting a stitching, a first layer, a second layer, a third layer, a fourth layer, a fifth layer, a sixth layer, and a seventh layer,
wherein the first layer is innermost,
wherein the seventh layer is outermost,
wherein the second layer extends between the first layer and the third layer,
wherein the fourth layer extends between the third layer and the fifth layer,
wherein the sixth layer extends between the fifth layer and the seventh layer,
wherein the stitching extends through the first layer, the second layer, the sixth layer, and the seventh layer,
wherein the stitching avoids extending through the third layer, the fourth layer, and the fifth layer,
wherein the second layer is bonded or adhered to the third layer,
wherein at least two of the third layer, the fourth layer, or the fifth layer are encapsulated via a material that extends between the second layer and the sixth layer, and
wherein the material is U-shaped, C-shaped, or V-shaped.

13. The device of claim 12, wherein the material encapsulates the third layer, the fourth layer, and the fifth layer.

14. The device of claim 12, wherein the material extends between the fifth layer and the sixth layer.

15. The device of claim 12, wherein the stitching avoids extending through the material.

16. The device of claim 12, wherein the material and the stitching define a gap therebetween, wherein the gap extends between the second layer and the sixth layer.

17. A method comprising:
causing an incontinence underwear to include a crotch area hosting a stitching, a first layer, a second layer, a third layer, a fourth layer, a fifth layer, a sixth layer, and a seventh layer, wherein the first layer is innermost, wherein the seventh layer is outermost;
causing the second layer to extend between the first layer and the third layer such that the second layer is bonded or adhered to the third layer;
causing the fourth layer to extend between the third layer and the fifth layer;
causing the sixth layer to extend between the fifth layer and the seventh layer;
causing the stitching to extend through the first layer, the second layer, the sixth layer, and the seventh layer and avoid extending through the third layer, the fourth layer, and the fifth layer;
encapsulating at least two of the third layer, the fourth layer, or the fifth layer via a material that extends between the second layer and the sixth layer, wherein the material is U-shaped, C-shaped, or V-shaped.

* * * * *